(12) United States Patent
Marsh

(10) Patent No.: US 10,973,410 B2
(45) Date of Patent: Apr. 13, 2021

(54) PORTABLE PHYSIOLOGY MONITOR

(71) Applicant: Inova Design Solutions Ltd, London (GB)

(72) Inventor: Leon Marsh, London (GB)

(73) Assignee: Inova Design Solutions Ltd, London (GB)

( * ) Notice: Subject to any disclaimer, the term of this patent is extended or adjusted under 35 U.S.C. 154(b) by 23 days.

(21) Appl. No.: 15/529,103

(22) PCT Filed: Nov. 25, 2015

(86) PCT No.: PCT/GB2015/053598
§ 371 (c)(1),
(2) Date: May 24, 2017

(87) PCT Pub. No.: WO2016/083807
PCT Pub. Date: Jun. 2, 2016

(65) Prior Publication Data
US 2017/0258329 A1    Sep. 14, 2017

(30) Foreign Application Priority Data

Nov. 25, 2014  (GB) ..................... 1420945

(51) Int. Cl.
*A61B 5/00* (2006.01)
*A61B 5/01* (2006.01)
(Continued)

(52) U.S. Cl.
CPC .............. *A61B 5/0024* (2013.01); *A61B 5/01* (2013.01); *A61B 5/0205* (2013.01);
(Continued)

(58) Field of Classification Search
None
See application file for complete search history.

(56) References Cited

U.S. PATENT DOCUMENTS 6,556,852 B1  4/2003  Schulze et al.
7,394,909 B1  7/2008  Widmer et al.
(Continued)

FOREIGN PATENT DOCUMENTS

EP  1777504 A1  4/2007
EP  2161556 A1  3/2010
(Continued)

OTHER PUBLICATIONS

International Search Report and Written Opinion PCT/GB2015/053598 dated May 10, 2016.
(Continued)

*Primary Examiner* — Kaylee R Wilson
*Assistant Examiner* — Jay B Shah
(74) *Attorney, Agent, or Firm* — Banner & Witcoff, Ltd.

(57) ABSTRACT

Wearable devices capable of measuring a core body temperature and other vital signs of a user in a range of situations are described herein. The wearable device is arranged to be retained within the ear canal of the ear, in order to prevent the wearable device from inadvertently removing itself from the ear. Providing an infrared thermopile at the innermost end of the ear insert ensures that the infrared thermopile is provided as close as possible to the tympanic membrane which will be used to provide an indication of the core body temperature.

18 Claims, 6 Drawing Sheets

(51) Int. Cl.

| | | |
|---|---|---|
| *G01J 5/02* | (2006.01) | |
| *A61B 5/0205* | (2006.01) | |
| *A61B 5/021* | (2006.01) | |
| *A61B 5/145* | (2006.01) | |
| *G01J 5/04* | (2006.01) | |
| *G01J 5/12* | (2006.01) | |
| *G01J 5/00* | (2006.01) | |
| *G01J 5/08* | (2006.01) | |
| *A61B 5/11* | (2006.01) | |
| *A61B 5/333* | (2021.01) | |

(52) U.S. Cl.
CPC ............ *A61B 5/1118* (2013.01); *A61B 5/333* (2021.01); *A61B 5/6817* (2013.01); *G01J 5/0011* (2013.01); *G01J 5/0215* (2013.01); *G01J 5/049* (2013.01); *G01J 5/0806* (2013.01); *G01J 5/12* (2013.01); *A61B 5/02125* (2013.01); *A61B 5/14542* (2013.01); *A63B 2230/50* (2013.01)

(56) References Cited

U.S. PATENT DOCUMENTS

| | | |
|---|---|---|
| 2002/0143242 A1 | 10/2002 | Nemirovski |
| 2004/0079888 A1* | 4/2004 | Inamura ................... G01J 5/02 250/353 |
| 2005/0043630 A1 | 2/2005 | Buchert |
| 2006/0045297 A1 | 3/2006 | Haussmann |
| 2008/0234600 A1* | 9/2008 | Marsh ...................... A61B 5/01 600/549 |
| 2011/0106484 A1* | 5/2011 | Quinn ...................... A61B 5/01 702/135 |
| 2012/0203077 A1 | 8/2012 | He et al. |
| 2013/0035607 A1 | 2/2013 | Wada et al. |
| 2013/0218022 A1 | 8/2013 | Larsen et al. |
| 2014/0051939 A1 | 2/2014 | Messerschmidt |
| 2014/0152970 A1 | 6/2014 | Wada et al. |

FOREIGN PATENT DOCUMENTS

| | | |
|---|---|---|
| GB | 2411719 B | 2/2008 |
| JP | 2005334254 A | 12/2005 |
| WO | 03/088841 A2 | 10/2003 |
| WO | 2005084531 A1 | 9/2005 |
| WO | 2006/091106 A1 | 8/2006 |
| WO | 2013/123626 A1 | 8/2013 |

OTHER PUBLICATIONS

Combined Search and Examination Report under Sections 17 and 18 (3)/ GB1420945.6/ dated Jan. 23, 2015.
UKIPO Examination Report/ GB1420945.6/ dated Oct. 5, 2015.
UKIPO Examination Report/ GB1420945.6 / dated Nov. 18, 2015.
UKIPO Examination Report/ GB1420945.6/ dated Jun. 3, 2016.
Combined Search and Examination Report/ GB1520836.6/ dated May 23, 2016.
UKIPO Examination Report / GB1520836.6/ dated Jan. 26, 2017.
UKIPO Examination Report / GB1520836.6/ dated Apr. 20, 2017.

* cited by examiner

PORTABLE PHYSIOLOGY MONITOR

CROSS-REFERENCE TO RELATED APPLICATIONS

This application is a U.S. National Stage application under 35 U.S.C. § 371 of International Application PCT/GB2015/053598 (published as WO/2016/083807 A1), filed Nov. 25, 2015, which claims the benefit of priority to GB 1420945.6, filed Nov. 25, 2014. Benefit of the filing date of each of these prior applications is hereby claimed. Each of these prior applications is hereby incorporated by reference in its entirety.

This invention relates to a physiology monitor and in particular to a wearable portable multi-parameter monitor for use during ambulatory and non-ambulatory applications.

BACKGROUND

Individuals may suffer heat, cardiac and respiratory related illnesses when exercising or operating in harsh environments, or if they are not able to respond to their body's changes in physiology due to being physically or mentally compromised.

Various monitoring apparatus are used in healthcare, sports medicine research and occupational welfare to monitor vital sign parameters, but for accurate monitoring of vital signs these monitors typically are limited to non-ambulatory use and so do not lend themselves to a wide range of potential applications where continuous monitoring of vital signs during ambulatory use would be desirable.

Sport

In sport, and more particularly professional sport and athletics, international competition is the ultimate challenge to the various regulatory systems of the body: physiological; biochemical; biomechanical and psychological. Professional and elite athletes constantly strive to improve performance where every millisecond counts. In sport medicine, a physiologist may measure body parameters such as core body temperature, heart rate, hydration status, VO2 max (maximal aerobic capacity) and lactate threshold to evaluate physical condition, help to inform strategies, and as part of a research activity. These parameters can be measured in the laboratory but this level of monitoring is not possible in the competitive environment of the field where, unlike a controlled setting, environmental conditions, terrain and psychological drivers are constantly changing. This limitation is due to invasive techniques being used, such as blood sampling or probes entering the body, and/or impracticalities of apparatus having wires connected to a diagnostics machine, logger or computer, and the size and weight of some apparatus.

In the consumer sports market, heart rate monitors have been around since the 1980's and are widely adopted amongst sports users as they strive to improve their fitness levels. There has recently been a rapid expansion of the fitness monitor wearables market with the likes of Fitbit and Jawbone wrist bands which only monitor activity, such as speed, distance, calorific burn rate, steps taken and cadence. There has also been a convergence of activity and heart rate monitoring with smart watches. Traditionally heart rate has been measured using chest straps detecting the electric pulses of the heart, but there can be reliability issues where the contacts do not have sufficient contact to the skin. Smart watches use the pulse oximetry technique where a tight strap is required to detect pulse from wrist area, which is at the periphery of the cardiovascular system. Whilst these devices measure heart rate with some success, no other vital sign parameters can be monitored today using mass market products.

Healthcare

In critical care, multiple devices are used to provide vital sign parameter sensing, some of which are very invasive. Vital sign parameters commonly measured are core body temperature, heart rate, blood pressure, oxygen saturation level, and respiration rate. With the emergence of telehealth services (aimed to help people with long-term chronic conditions to live independently in their own home), new requirements in health management have highlighted the need for remote patient monitoring to enable early intervention and prevent exacerbations and hospital admissions/re-admissions. For example, each year in the UK alone, there are around 159,000 deaths from cardiovascular disease (source: British Heart Foundation, 2011), 30,000 deaths from hypothermia (source: BBC News, 2013) and 25,000 deaths from chronic obstructive pulmonary disease (COPD) (source: NHS Choices, 2013).

The risk is compounded by issues common among the elderly due to diminished physiological mechanisms and cognitive functions, lack of mobility, the prevalence of comorbidities, and the widespread use of medications with physiological side-effects.

The risk is further compounded with Individuals with mental illness, particularly since mental illnesses are common with elderly people. Mental health patients are further at risk of illness due to failures in detection and appropriate management in care, for example, the specific interventions for improving oral hydration in older people with dementia remain poorly studied and understood. There is a tremendous opportunity to improve health outcomes and reduce costs across the health care system if vulnerable elderly individuals can be easily and conveniently assessed and given prompt, appropriate care at the point of need.

Newborns, infants and children up to 4 years of age are especially sensitive to the effects of high temperatures and rely on others to regulate their environments and provide adequate liquids. They are at risk of heat illness compared to adults because their thermoregulatory systems are less efficient; they produce more heat (because of a greater surface area-to-body mass ratio); are less likely to drink adequate fluids during exercise and in heat; their body temperatures warm at a rate of 3 to 5 times faster; they sweat less; they have a higher metabolic rate; and their inability to care for themselves and control their environment. Other risk factors for children developing heat illness are: lack of exercise; being overweight or obese; being developmentally delayed or having cognitive disabilities; and those having underlying medical conditions (diabetes) are at higher risk.

Young children are also more likely to dehydrate than adults as the turnover of fluids and solutes can be as much as 3 times that of adults. Dehydration is one of the leading global causes of morbidity and mortality among children. Around the world, an estimated 8,000 children younger than 5 years old die each day due to gastroenteritis and dehydration. Gastroenteritis alone accounts for around 10% of all pediatric hospital admissions.

Military Personnel, Fire Fighters and First Responders

Military personnel and people working in the fire service and other first responders must wear personal protective equipment (PPE) to protect themselves from hazardous threats such as chemical agents, gases, fire, small arms and even Improvised Explosive Devices (IEDs). This PPE can include a range of hazmat suits, firefighting turnout gear, body armor and bomb suits, among many other forms.

Depending on its design, PPE often encapsulates the wearer from a threat and creates a microclimate, due to an increase in thermal resistance and ineffective sweating mechanism. This is compounded by increased work rates, high ambient temperatures and humidity levels, and direct exposure to the sun. The net effect is that protection from one or more environmental threats inadvertently brings on the threat of heat and cardiovascular stress.

In cases where this stress is caused by physical exertion, hot environments or wearing PPE, it can be prevented or mitigated by taking frequent rest breaks, staying hydrated and carefully monitoring body temperature and heart rate. However, in situations demanding prolonged exposure to a hot environment or wearing PPE, a personal cooling system is required as a matter of health and safety. For example, soldiers traveling in combat vehicles can face microclimate temperatures in excess of 150 degrees Fahrenheit and require a vehicle-powered cooling system.

Every year there are deaths of service personnel during training and operational tours. The highly publicised deaths of 3 UK SAS soldiers in July 2013 whilst training in the Brecon Beacons was a reminder of this. The soldiers died due to heat stroke. In fact each year there are approximately 1,900 US soldiers (source: Heat illness: Prevention is best defence, www.army.mil, 2010) and 300 UK soldiers (source: Ministry of Defence, 2013) who receive medical treatment for heat illness. There are also cardiovascular illnesses: 1 in 12 US soldiers who died in the Afghanistan and Iraq had heart disease, and a quarter of these were severe cases (source: Daily News, 2012).

In the Fire Service, risks are compounded by the fact that firefighters are exposed to extreme environmental heat while wearing PPE, and inevitable dehydration and warming can have critical, detrimental and fatal effects on the thermoregulatory and cardiovascular systems of the body.

Thus it is apparent that measuring one or more of the various vital signs would have utility in a variety of settings. Some of the currently available techniques for monitoring these vital signs in various settings will now be described.

Monitoring Core Body Temperature

The goal of thermometry is to measure core body temperature which is the temperature of the vital organs, hence it is important to identify the parts of the body that most closely reflect the temperature of those organs. Core temperature can be measured at the rectum; intestines; esophagus; ear; bloodstream; tissue; and skin (including armpit).

Traditionally, in acuity care areas, temperatures have been measured using mercury-in-glass thermometers, orally. This method is considered effective in healthcare but is influenced by many external and environmental variables including eating, drinking and breathing. In addition, concerns are growing about the health and safety risks, such as glass breakage and the potential for mercury poisoning. Mercury-in-glass thermometers have been implicated in episodes of cross-infection and outbreaks of diarrhoea. It is not suitable for use for during exercise due to the risk of the glass breakage and mercury poisoning.

Rectal thermometers are invasive, uncomfortable, limit movement and sometimes effort, often experience a lag behind true c.b.t., have a risk of cross contamination, are affected by the temperature of fluid and food ingested, and are currently restricted to use in a laboratory. Esophageal thermocouples are not popular because of the difficulty of inserting the thermistor, irritation to the nasal passages and general subject discomfort during monitoring. Pulmonary artery catheters are extremely invasive and are not suitable for use during exercise.

The intestinal radio pill measures the temperature of the abdomen when ingested and wirelessly transmits core body temperature to a Data Recorder worn on the outside of the body as it travels through the digestive tract. These are very costly since the pills are disposable. Similarly to rectal thermometers, they are affected by the temperature of fluid and food ingested and experience a lag behind true c.b.t. (which can be found nearest the hypothalamus in the brain).

Skin thermocouples are far away from the core so not appropriate for core temperature measurements. Electronic thermometers take readings from the axilla or orally and use an algorithm to calculate the temperature, but these are not always considered to be clinically accurate.

Tympanic ear thermometers measure the infrared temperature of the tympanic membrane (eardrum). Ear thermometers accurately reflect core body temperature, since the eardrum shares blood supply with the temperature control centre in the brain, the hypothalamus. Therefore, changes in core temperature are reflected sooner or more accurately in the ear than at other sites. They are becoming increasingly popular as a method for measuring core body temperature, especially in home healthcare environments and in use on infants since they are very safe to use and considered to be medically accurate. At present, ear thermometers available in the market are only designed for recording single measurements and are not wearable. Typically an ear thermometer includes a thermopile that is held in position at the opening of the ear canal by the medical practitioner and aligned using a horn that is temporarily inserted into the entrance of the ear canal. As a result, repeatability can be unreliable, time consuming, disruptive to activity and lead to cross-contamination. General limitations of all of these devices are that they usually require more than one person to operate them since they are often dependent on additional apparatus; require in-depth knowledge to use them effectively or at all; are often too complex to operate whilst carrying out activity; do not always offer continuous monitoring and most are non-ambulatory.

International patent application publication number WO2005084531 discloses a hydration monitor comprising an earpiece having a temperature sensor for measuring a subject's core body temperature via the tympanic membrane. The earpiece is set in the concha in use and positions the temperature sensor in the canal at the open end of the ear canal. The earpiece is retained in position primarily by a clip over the pinna of the ear in use.

Monitoring Pulse Rate, Pulse Pressure and Oxygen Saturation Levels

Pulse in the upper body can be taken at the temple, neck, ear or chest. The two common methods of measuring pulse are via an electrocardiogram (ECG) and pulse oximetry.

Pulse oximetry can be measured through light absorbance or a photoplethysmograph (PPG). Pulse oximetry through light absorbance involves red and near infrared light being transmitted through a relatively thin tissue bed, such as the ear or finger, where the ratio of red to infrared light transmitted or reflected is a measure of the relative amounts of haemoglobin and oxyhaemoglobin in the blood. A pulse is detected since the absorbance effects of these amounts are different. A pulse oximetry sensor can also be used to determine oxygen saturation Most pulse oximeters on the market feature a PPG, which oscillates due to a change in blood volume with each heartbeat, thereby detecting a pulse. The basic form of PPG technology is simpler than pulse oximetry, requiring only a few components and less complicated control of the driving circuitry. Transmission PPG can be used at the ear to gather PPG data, or reflectance PPG sensors can be used at the forehead above the eyebrow or at the temple. Possible sites for measuring pulse with a PPG sensor in during activity or inactivity are the wrist, finger, hand, ear, shoulder, or temple.

Pulse can also be determined from other methods, such as an ECG. An ECG uses electrodes spaced over the body to detect the electrical activity of the heart. The heart rate monitor transmitter developed for sport applications uses two electrodes to detect the voltage differential on the skin during every heart beat and sends the signal continuously and wirelessly to the wristwatch receiver. While these devices are commonly used for monitoring heart or pulse rate, there is currently no device available for monitoring other indicators of potential heat stroke, such as temperature, and no method of determining an onset of heat illness.

Monitoring Respiration Rate

Respiration rate is regarded as the invisible vital sign. Deviations from normal respiration rates are well established predictors of adverse outcomes, and indicate the response to treatment. It can be used to monitor or detect various conditions including respiration conditions such as asthma, trauma to the chest or shock, metabolic acidosis including renal failure and sepsis, and central respiration drive including head injury, neurological illness and neuromuscular illness.

Respiration rate is badly recorded in hospitals as it is not automated to the same degree as other vital signs. Current methods of determining respiration rate are: snorkel masks where a freely moving element in a pipe connected to the mask signifies each breath and is counted over a sixty second period by nursing staff to arrive at a measure of breaths per minute; sensors on masks which add weight to a lightweight device; sensors on the torso where the signal typically suffers from background noise; and sensors on beds which are costly.

BRIEF SUMMARY OF THE DISCLOSURE

In accordance with one aspect of the present invention there is provided a wearable device for measuring a tympanic temperature. The device comprises an ear insert. The ear insert comprises a retaining portion configured to be retained within an ear canal and provided with an infrared thermopile at an innermost end of the ear insert, arranged for measuring a tympanic temperature in use, and a reflector arranged to reflect infrared signals from a tympanic membrane onto a sensitive surface of the infrared thermopile.

Thus, a field of view of the infrared thermopile can be focused onto the tympanic membrane.

The reflector may be a concave reflector. The reflector may be a mirror.

The sensitive surface of the infrared thermopile may be arranged to be positioned substantially parallel to the ear canal in use. The sensitive surface of the infrared thermopile may be arranged to be positioned substantially perpendicular to the tympanic membrane in use.

The retaining portion may be formed from a bulk material and may be configured to extend along and substantially fill the ear canal in use. The ear insert may further comprise an infrared thermopile module comprising a housing supporting the infrared thermopile. The ear insert may further comprise a wired electrical connection extending through the ear insert for outputting a signal from the infrared thermopile in use, and an audio conduction channel, provided by an audio passageway defined at least partially within the ear insert and configured as a waveguide to relay sound to the innermost end of the ear insert. An output of the audio passageway may be provided at an innermost end of the ear insert, arranged to open in the ear canal towards the tympanic membrane, in use.

This in itself is believed to be novel, and so, in accordance with another aspect of the present invention, there is provided a wearable device for measuring a tympanic temperature. The device comprises an ear insert. The ear insert comprises a retaining portion formed to extend along, substantially fill and be retained within an ear canal in use; a thermopile module comprising a housing supporting an infrared thermopile arranged at an innermost end of the retaining portion and arranged for measuring a tympanic temperature in use; a wired electrical connection extending through the ear insert for outputting a signal from the infrared thermopile in use; and an audio conduction channel, provided by an audio passageway defined at least partially within the ear insert and configured as a waveguide to relay sound to the innermost end of the ear insert. An output of the audio passageway is provided at an innermost end of the ear insert, arranged to open in the ear canal towards the tympanic membrane, in use.

Thus, a wearable device is provided capable of accurately measuring core body temperature from a thermopile positioned at or near a second bend of the osseous, from which it is possible to obtain a direct line of sight to the whole or a substantial part of the tympanic membrane. The wearable device is also capable of providing sound to the tympanic membrane through the ear insert, increasing the comfort of the wearable device for the user.

The audio passageway may at least partially surround the wired electrical connection. The audio passageway may completely surround the wired electrical connection.

The retaining portion may be configured to substantially centralise the thermopile module within the ear canal. The retaining portion may be configured to substantially direct the thermopile module towards the tympanic membrane.

The audio passageway may be defined substantially concentrically within the retaining portion.

The wired electrical connection may be a flexible PCB. The wired electrical connection may be an umbilical cable.

The audio passageway may be defined partially within the thermopile module. Thus, the output of the audio passageway may be provided in the housing of the thermopile module.

The audio passageway may be configured as a passive waveguide to relay sound from an audio driver or an ambient environment.

The audio conduction channel may comprise an audio driver electrically connected to an audio input configured to drive the audio driver to output sound and coupled to the audio conduction channel.

The wearable device may further comprise a microphone arranged to receive sound from outside the ear. The audio input may be provided by a signal derived from the microphone.

The present disclosure provides a wearable device for measuring a tympanic temperature. The device comprises an ear insert configured to be retained within an ear canal and provided with an infrared thermopile at an innermost end of the ear insert.

Thus, there is provided a wearable device capable of measuring a core body temperature of a user in a range of situations. The wearable device is arranged to be retained within the ear canal of the ear, in order to prevent the wearable device from inadvertently removing itself from the ear. Providing an infrared thermopile at the innermost end of the ear insert ensures that the infrared thermopile is provided as close as possible to the tympanic membrane which will be used to provide an indication of the core body temperature. This configuration ensures that more infrared radiation is incident on the infrared thermopile compared to models having a thermopile sensor positioned away from the innermost end of any ear inserts.

A shape of the ear insert may be pre-configured to retain the ear insert within the ear canal. Thus, the ear insert may be manufactured to match a pre-scanned ear canal shape, and may be individually shaped for the user. The shape of the ear insert may substantially complement a shape of the ear canal.

A shape of the ear insert may be deformable to retain the ear insert within the ear canal. Thus, the ear insert may be formed from deformable material which is arranged to deform when inserted into the ear. The deformable material may provide a fit which is almost as good as, as good as, or better than the fit achieved with the pre-configured shape. The shape of the ear insert may be deformable to complement a shape of the ear canal.

The ear insert and infrared thermopile may each be configured such that the infrared thermopile, in use, receives infrared signals from a tympanic membrane.

The ear insert may comprise a reflector arranged to reflect infrared signals from the tympanic membrane onto a sensitive surface of the infrared thermopile. Thus, the infrared thermopile need not be positioned directly facing the target area from which infrared signals are being emitted.

The reflector may be a concave reflector. Thus, the active surface of the infrared thermopile need not be as large as the target area from which infrared signals are being emitted. Alternatively, the concave reflector can be used to focus the infrared signals down so that even a relatively insensitive infrared thermopile may be used to detect the infrared radiation emitted in the inner ear. The reflector may be a mirror.

The sensitive surface of the infrared thermopile may be arranged to be positioned substantially parallel to the ear canal. Thus, the infrared thermopile need not be the only sensor positioned near the innermost end of the ear insert. Alternatively, a PCB on which the infrared thermopile may be mounted need not have any flexible connections, which would increase manufacturing complexity, and so cost of the wearable device.

The ear insert may comprise an audio conduction channel between an outside of the device and the innermost end of the ear insert, configured to allow a sound to pass from outside the device into the ear through the ear insert. Thus, sound from outside the device may still be heard by the same ear in which the wearable device is inserted. Even in cases where there is a seal provided around the ear insert, sound may still propagate.

The audio conduction channel may be a passive waveguide. The audio conduction channel may allow the passage of air and moisture. This allows for ambient heat and moisture transfer out of the device. This is particularly beneficial where the user is conducting strenuous activity, such as exercise.

The audio conduction channel may comprise an audio driver electrically connected to an audio input and configured to drive the audio driver to output the sound.

The audio input may be provided by a microphone arranged to receive sound from outside the ear. Thus, the audio conduction channel is, in some embodiments, an electrical communication channel, and not a physical channel at all.

A sealing member may surround a boundary of the ear insert to substantially prevent air passing through a region between the ear insert and the ear canal.

A shape of the ear insert may be formed at least partly by the sealing member.

The wearable device may further comprise an outer portion arranged to be provided outside the ear canal, wherein at least a part of the outer portion is arranged to be adjacent to a concha region of the ear. Thus, the wearable device may comprise more than merely an ear insert. Some part of the wearable device may protrude outside the ear canal. By positioning part of the outer portion adjacent to the concha, further sensors may be provided on the wearable device to detect parameters of the body which are detectable from the concha region of the ear.

The wearable device may further comprise a pulse oximetry sensor configured to measure at least one of: a pulse rate, a pulse volume, and an oxygen saturation level.

The pulse oximetry sensor may be provided in the outer portion of the device. Thus, the pulse oximetry sensor may be arranged to measure properties of blood vessels in a part of the ear outside the ear canal The wearable device may further comprise an ECG sensor comprising a first electrode and a second electrode. Thus, at least a 1-lead ECG monitor may be provided.

The first electrode may be provided on either the outer portion or the ear insert and arranged to be in contact with the ear. The second electrode may be provided on either an outer portion or an ear insert of a further wearable device, or may configured to be provided behind, below or in front of the ear. Thus, the electrodes of the ECG sensor may be positioned in various positions relative to one or both ears.

The wearable device may further comprise a respiration sensor. The respiration sensor may be provided at an innermost end of the ear insert. The respiration sensor may be arranged to be provided behind or in front of the ear, such that breathing vibrations can be measured via a jaw bone. The respiration sensor may be positioned against the concha.

The wearable device may be physically coupled to an acceleration sensor configured to measure an indication of a movement of the device.

In some embodiments, the wearable device may comprise both an acceleration sensor and a pulse oximetry sensor. Thus, the wearable device may be configured to measure blood pressure and respiration rate.

The wearable device may further comprise a transceiver configured to transmit a sensor signal to a further device, wherein the sensor signal is based on the measurements of at least one of the infrared thermopile, the pulse oximetry sensor, the ECG sensor, the respiration sensor and the acceleration sensor. Thus, the device is arranged to output data analysable by a further device.

The wearable device may be in the form of an earpiece. The wearable device may be in the form of a personal physiological monitoring device or a physiology monitor.

In a preferred embodiment of the present invention, a physiology monitor is arranged to also comprise a pulse sensor for continuously measuring any one of, or a combination of, a subject's pulse rate, pulse volume, oxygen saturation level and respiration rate, the processor being arranged to accept measurements from the pulse sensor and calculate changes in the measured pulse rate, pulse pressure, pulse volume, oxygen saturation level and respiration rate.

In a preferred embodiment of the present invention, a physiology monitor may be arranged to further comprise an electrocardiography (ECG) sensor for continuously measuring a subject's ECG, the processor being arranged to accept measurements from the ECG sensor and calculate changes in the measured ECG.

In a preferred embodiment of the present invention, a physiology monitor may be arranged to further comprise a dedicated respiration sensor for continuously measuring a subject's respiration rate, the processor being arranged to accept measurements from the respiration sensor and calculate changes in the measured respiration rate, as well as or instead of the respiration rate which may be determined by the pulse sensor.

In a preferred embodiment of the present invention, a physiology monitor may be arranged to further comprise a motion sensor for continuously measuring a subject's movement and orientation, the processor being arranged to accept measurements from the motion sensor and calculate changes in the measured movement and orientation.

In a preferred embodiment of the present invention, a physiology monitor may be arranged to measure ballistocardiography (BCG), the processor being arranged to accept measurements from the motion sensor and calculate changes in BCG which indicates changes in heart rate.

In a preferred embodiment of the present invention, a physiology monitor may be arranged to measure pulse transit time (PTT), the processor being arranged to accept measurements from a combination of two or more of the pulse sensor, motion sensor (BCG) and ECG sensor, and calculate changes in PTT. Pulse transit time is a measure of pulse wave velocity, which in turn is an estimation of relative blood pressure. A blood pressure cuff may be used in addition to PTT measurements to calibrate the diastolic and systolic PTT measurements and provide an estimation of absolute blood pressure.

In a preferred embodiment of the present invention, a physiology monitor may be arranged to measure hydration status, the processor being arranged to accept measurements from the temperature sensor and calculate changes in the measured temperature to determine changes in hydration status (according to patent application GB2411719B).

In a preferred embodiment of the present invention, a physiology monitor may be arranged to measure a subject's sedation and/or anaesthesia level, the processor being arranged to accept measurements from any one of, or a combination of, the temperature sensor, pulse sensor, respiration sensor and motion sensor and calculate changes in the sedation and/or anaesthesia level.

In a preferred embodiment of the present invention, a portable physiology monitor is arranged to continuously measure any one of, or a combination of, core body temperature, pulse rate, pulse pressure (PTT), pulse volume, oxygen saturation level, ECG, respiration rate, hydration status, sedation level, anaesthesia level, and movement (including BCG) and orientation non-invasively. All of these physiological parameters are monitored in real time, and measurements are output via a display and/or audio feedback to the subject, clinician or support individual. In this manner a subject, clinician or other individual can see and/or hear the current and changing status of their/the subject's physiological parameters. Through monitoring or detecting relative changes in these parameters in a healthcare setting the subject/clinician/supporting individual can determine health status, the onset of adverse health conditions and reactions to treatment. In ambulatory defence and sport applications, relative changes can determine fitness status, athletic performance changes, fatigue, the onset of illness, and help monitor recovery from illness and acclimation state when introduced into new environments.

The present invention is particularly useful in the areas of healthcare, occupational welfare and sport. Incorporating the measurement of all aforementioned physiological and vital sign parameters into one convenient, lightweight, wireless and non-invasive multi-parameter device has significant advantages over prior art, where almost all of the parameters are currently measured by separate devices, some of which are invasive and most of which are tethered by electrical cables.

The advantages for in-patient healthcare include: improved patient comfort and mobility since the present invention is designed to provide the monitoring of all vital signs in one small non-invasive wireless device; improved safety provided by the non-invasive technique, as opposed to prior art and in particular oesophageal probes which in rare cases can cause fatal perforations; better patient care, outcomes and reduced number of hospital visits and time in hospital as a result of earlier intervention due to continuous automated monitoring; a significant reduction in clinician and nursing staff time, and hence cost, and cross-contamination of infections as a result of only needing to fit the present invention with continuous automated monitoring on a patient once, as opposed to carrying out individual periodic measurements with prior art; and a further reduction in cost through not having to acquire or replace multiple single-parameter prior art apparatus to measure all vital signs of one patient. In the telehealth setting, recovering or chronically ill patients will also receive improved care through remote monitoring at home or in a care home to ensure timely intervention when necessary, which in turn will reduce emergency incidence rates and re-admissions and their associated cost and resource burden on the national health system, as well as enable more individuals to live an independent life at home.

A further example of the benefit of the present invention is providing more timely and improved accuracy of diagnosis of conditions which have symptoms affecting multiple vital sign parameters, such as sepsis or a stroke. Sepsis has symptoms which can develop quickly including a high temperature, a fast heart beat and fast breathing. A stroke involves compromised blood supply to the brain. Detecting changes in heart rate, ECG, blood pressure and oxygen saturation simultaneously would increase the chances of determining the onset of stroke early and preventing long term consequences.

In occupations such as the fire service and the military, through monitoring all vital sign parameters simultaneously, providing real-time feedback and enabling intervention, the present invention will prevent illness and mortality from thermoregulatory, cardiac and respiratory failure, especially whilst operating in harsh environments. Since dehydration affects both the thermoregulatory and cardiovascular systems, the present invention will enable quicker diagnosis of an individual with severe dehydration which will drastically reduce the chance of heat stroke and fatal consequences. It will also provide useful information about the activity profile of personnel and in training could be used to improve, and monitor improvements in, fitness and performance.

In sport, whilst the present invention will be vital in preventing the same conditions as with occupational workers in much larger volumes of subjects, it is predicted to have a larger role serving as a training aid to improve fitness, performance and wellness.

In a preferred embodiment, the portable physiology monitor includes an earpiece or headset containing any one of, or a combination of, a thermopile sensor to measure core body temperature via the tympanic membrane (eardrum) and/or temporal artery; a pulse oximetry sensor(s) to measure pulse rate, pulse volume, oxygen saturation and respiration via the ear; at least two electrode sensors to measure ECG; a microphone to measure respiration rate via bone conduction vibrations and/or via breath; an accelerometer to measure movement, orientation and BCG; combinations of two or more of the pulse sensor, motion sensor (BCG) and ECG sensor to calculate changes in PTT; and a wristwatch, smartphone or other visual and/or audible indicator module that provides the subject and/or other individual with real-time feedback to inform them of their/the current and changing physiological parameters, and alert them to intervene at the onset of illness or at a more severe state of illness. If multiple sensors of the same type are included, the processor may be configured to average the multiple signals or supply data from the individual signals to the subject.

In a further embodiment, the system of the present invention may be configured such that a wristwatch or smartphone contains the pulse oximetry sensor, with all other sensors contained in the earpiece.

The thermopile sensor detects incident infrared radiation from the tympanic membrane and provides a voltage output equivalent to the core body temperature of the subject. This is then fed into an algorithm and the result is output via the indicator module. Preferably, the result is the core body temperature of the subject including any warnings of heat illness, as appropriate.

In a preferred embodiment, the voltage output of the thermopile sensor is fed into an additional algorithm according to patent application GB2411719B and the result is output via the indicator module. Preferably, the result is the hydration status of the subject including any warnings of dehydration.

In a preferred embodiment, the portable physiology monitor includes an electrical heater element to quickly equilibrate the temperature of the thermopile sensor to the approximate temperature of the auditory canal, immediately upon power start-up and prior to the first measurement, to stabilise the thermopile signal when the device is inserted into the auditory canal.

The pulse oximetry sensor monitors the oxygen saturation level of a subject's pulse through the transmittance of different wavelengths of light through tissue. A photodetector receives a corresponding ratio of the different wavelengths of light depending on the absorption of each wavelength and oxygen saturation level present, and provides an equivalent voltage output. This is then fed into an algorithm and the result is output via the indicator module. Preferably, the result is the pulse rate, pulse volume, oxygen saturation level and respiration rate of the subject, including the detection of heart rate variability/arrhythmias. In a further embodiment, the present invention may be configured to monitor the metabolism of oxygen, by measuring the absorption of light at several wavelengths, to distinguish between the percentages of oxygenated haemoglobin to total haemoglobin and determine adverse health conditions including oxygen deprivation (hypoxia), oxygen deficiency in arterial blood (hypoxemia) or oxygen deficiency at the tissue level.

As an alternative to, or in addition to, the pulse oximetry sensor, further embodiments of the present invention may incorporate a piezoelectric monitoring system for measuring pulse rate and pressure from the temporal artery. The system comprises a cuff to occlude the artery and a piezoelectric contact microphone to record and analyse the Korotkoff sounds from the changes in pulse, time and frequency domain.

When placed on the body at least two ECG electrodes measure the heart's electrical conduction system and detects electrical impulses generated by heart beats which provide a voltage equivalent to the waveform of the impulses. This is then fed into an algorithm and the result is output via the indicator module. Preferably, the result is an electrocardiogram of the subject.

The microphone detects and monitors vibrations from a subject's respiration via bone conduction of the skull and inner ear, and/or sound waves via a subject's breath, and provides a voltage equivalent to the amplitude of the vibrations and/or sound waves. This is then fed into an algorithm and the result is output via the indicator module. Preferably, the result is the respiration rate and profile of the subject including the monitoring and detection of adverse health conditions.

The accelerometer (3-, 6- or 9-axis) detects a subject's movement and position and provides equivalent data which is then fed into an algorithm and the result is output via the indicator module. Preferably, the result is the cadence, speed, distance, steps taken, orientation, calorific count, state of activity, level of activity, mobility, and/or circadian rhythm including the monitoring and detection of adverse health conditions. The accelerometer may be a 3-, 6- or 9-axis accelerometer and may be used in conjunction with or substituted for a gyroscope and/or magnetometer.

The accelerometer may also be used to determine BCG, an alternative method of measuring heart rate and a method to determine PTT, by measuring repetitive motions of the human body arising from the sudden injection of blood into the vessels with each heartbeat. The motion data is fed into an algorithm and the result is output via the indicator module and fed into the PTT algorithm.

Determined with a combination of PPG and BCG, or PPG and ECG, or all three for greatest accuracy, PTT may be measured to determine pulse wave velocity (PWV) which correlates to blood pressure (BP). PTT provides an estimation of relative BP, and requires calibration to obtain an estimation of absolute BP (diastolic and systolic values). Calibration may be provided with a BP cuff at the start of or during the monitoring session.

In a further embodiment of the present invention, a combination of PPG, data from the accelerometer, pulse oximetry sensor and/or dedicated respiration sensor may be used to establish maximal aerobic capacity (VO2 max) in exercising subjects.

Preferably, the earpiece includes one or more air flow channels to allow the flow of ambient air around the auditory canal and enable the subject to continue hearing ambient sound. To prevent an imbalance to hearing where there are no or insufficient air channels to allow the flow of ambient air and transfer of ambient sound, one or more external microphone(s), a speaker and the processor may be configured to accept measurements of ambient sound from the microphone(s) before transmitting sound waves or bone conduction vibrations from the speaker towards the subject's inner ear. The ambient sound may be amplified before being transmitted to the inner ear to improve a subject's hearing ability, in a similar manner to a conventional hearing aid. A digital signal processor (DSP) may be used to improve audio signal quality.

The primary and/or remote device may be configured to incorporate one or more standard or bone conduction microphone(s) in addition to a speaker to capture voice input and operate as a telephony device, including use as either a primary telephony device including associated antennas and circuitry, or a slave device to a primary telephony device where sound is received from the primary device and output to the subject via the slave device, or the subjects' voice is captured by the slave device and transmitted to the primary device. The primary and/or remote device may utilize one or more microphone(s) to also enable noise cancelation (isolation) to reduce environmental noise. The noise cancelling feature may be configured to be switchable by the subject to switch between music playback or communications and hearing the surrounding environment.

In alternative embodiments, the present invention may be configured as an individual earpiece providing aforementioned functions along with mono sound to the subject for communications/telephony and transfer or ambient sound to the user, or as a pair of earpieces to provide stereo sound to additionally transmit audio sound (music) to the subject's inner ear from music either stored locally on the earpiece or transmitted from a remote device.

Preferably, the portable physiology monitor earpiece is designed to stably fit within the subject's ear and maintain a constant position. For example, the sensors, processor and supporting electronics may be mounted within a malleable rubber or polyurethane member or similar to allow it to adaptably fit within different sized ears' of subjects. In another alternative, various sized ear pieces may be provided to allow the subject to select the best fit and comfort. In a further alternative, the earpiece may be custom moulded to the subject's ear for optimal fit and comfort.

Embodiments of the present invention could be used by almost all men and women, including the disabled. Various embodiments may eventually be produced to cater for the various needs of:
  a. Professional and amateur athletes and sportsmen/women (and novice sports persons);
  b. sports medicine research;
  c. exercise physiology;
  d. military personnel (Army, Royal Navy and Royal Air Force, special forces);
  e. police officers;
  f. firefighters;
  g. those in occupational health and at risk of exertional heat or cardiovascular illness (bakery workers, farmers, construction workers, miners, boiler room workers, factory workers);
  h. elderly and infirm;
  i. medical patients (inpatients and pre- or post-operative outpatients);
  j. healthcare telemedicine;
  k. mentally and chronically ill;
  l. domestic healthcare including all individuals;
  m. paediatrics; and,
  n. normal public subjects

BRIEF DESCRIPTION OF THE DRAWINGS

Embodiments of the invention are further described hereinafter with reference to the accompanying drawings, in which.

DETAILED DESCRIPTION

Figure 1:
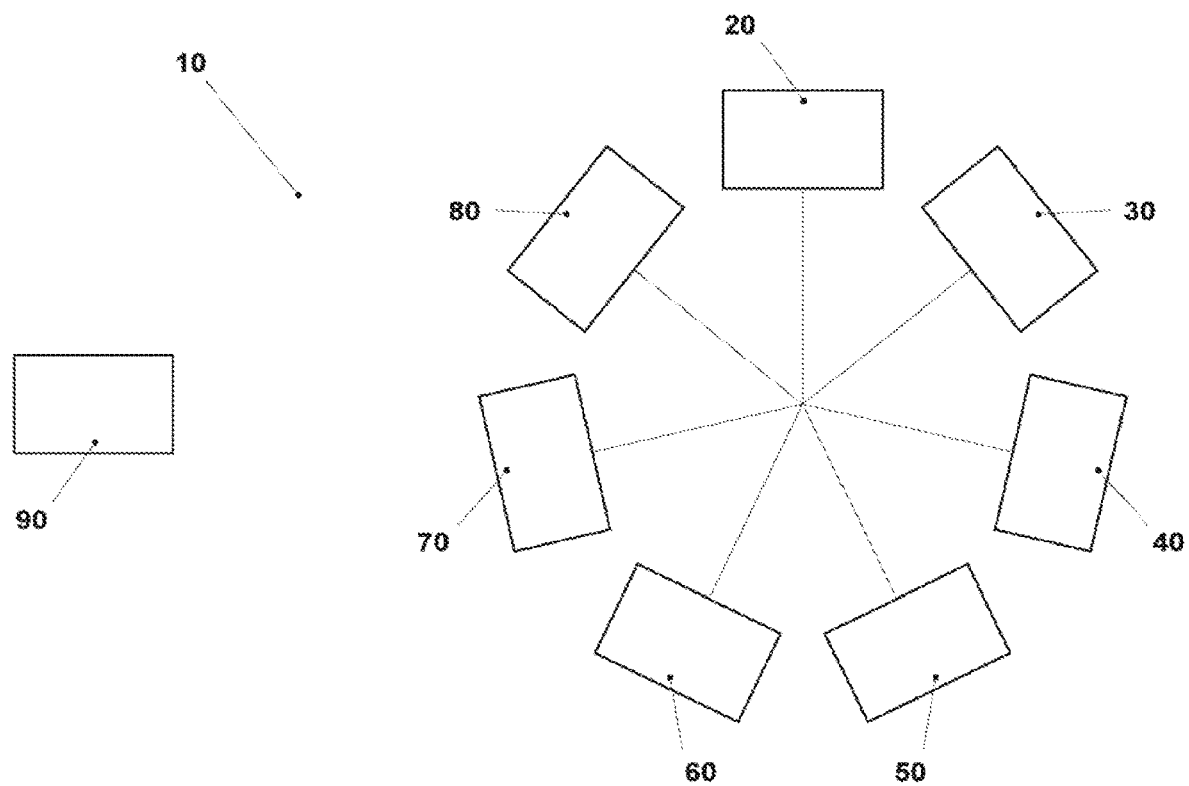
FIG. 1 is a block diagram of an embodiment of a portable physiology monitoring system.

FIG. 1 is a block diagram of an embodiment of a portable physiology monitoring system.

The portable physiology monitoring system 10 includes a temperature sensor 20, a pulse oximetry sensor 30, a respiration sensor 50, a motion sensor 60, a processor 70 and a display 90. Preferably, the portable physiology monitoring system also includes an ECG sensor 40 and a speaker 80.

The temperature sensor 20 is arranged to measure the core body temperature of a subject; the pulse oximetry sensor 30 is arranged to measure the pulse rate, pulse volume and oxygen saturation level of a subject; the ECG sensor 40 is arranged to measure the ECG of a subject; the respiration sensor 50 is arranged to measure the respiration rate of a subject; and the motion sensor 60 is arranged to measure the movement and orientation of a subject. All sensors are arranged to communicate the measured physiological parameters to the processor 70. Upon receipt of the measurements, the processor is arranged to output one or more of the parameters to the speaker 80 and/or display 90.

Figure 2:
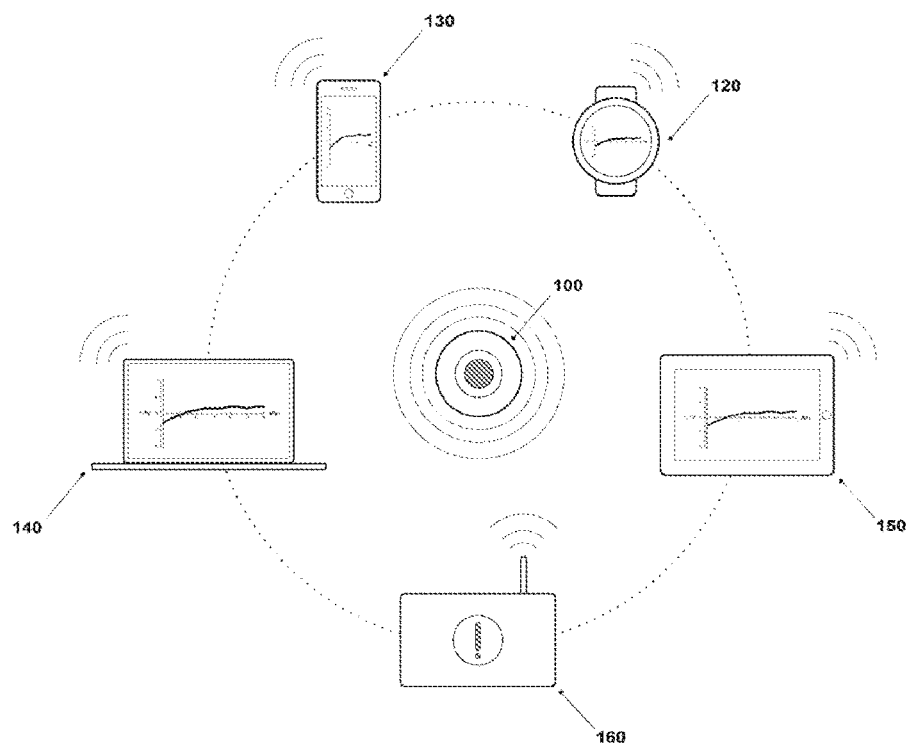
FIG. 2 is a schematic diagram of a portable physiology monitor product ecosystem incorporating the system of FIG. 1.

FIG. 2 is a schematic diagram of a portable physiology monitor product ecosystem incorporating the system of FIG. 1.

The earpiece 100 is arranged to communicate the physiological parameter measurements to remote common consumer wireless devices such as a smartwatch 120, smartphone 130, laptop or desktop computer 140 and computer tablet 150. For monitoring applications such as monitoring subjects or patients at home or in a nursing home, the earpiece 100 is also arranged to communicate the measurements to an internet enabled hub 160 which in turn communicates the measurements and/or alerts to a remote monitoring and response team positioned to support the subject or patient as required.

Figure 3:
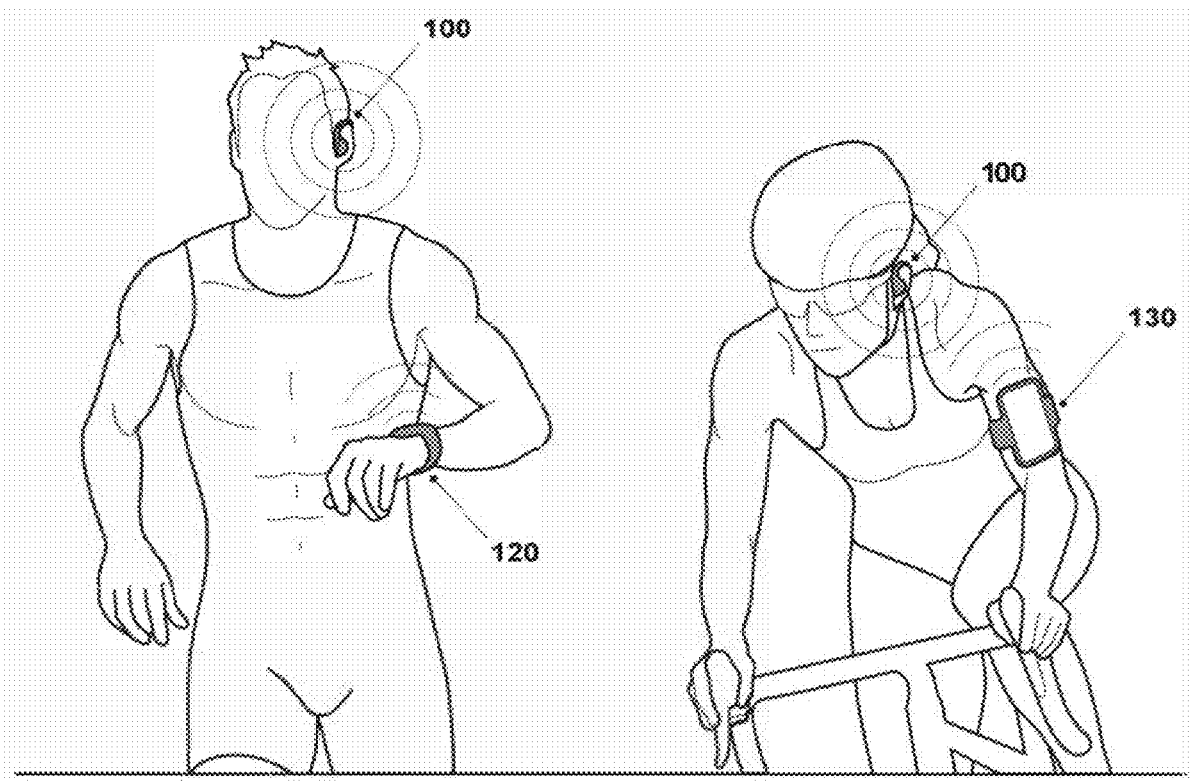
FIG. 3 is a schematic diagram of a portable physiology monitor incorporating the system of FIG. 1.
Figure 4:
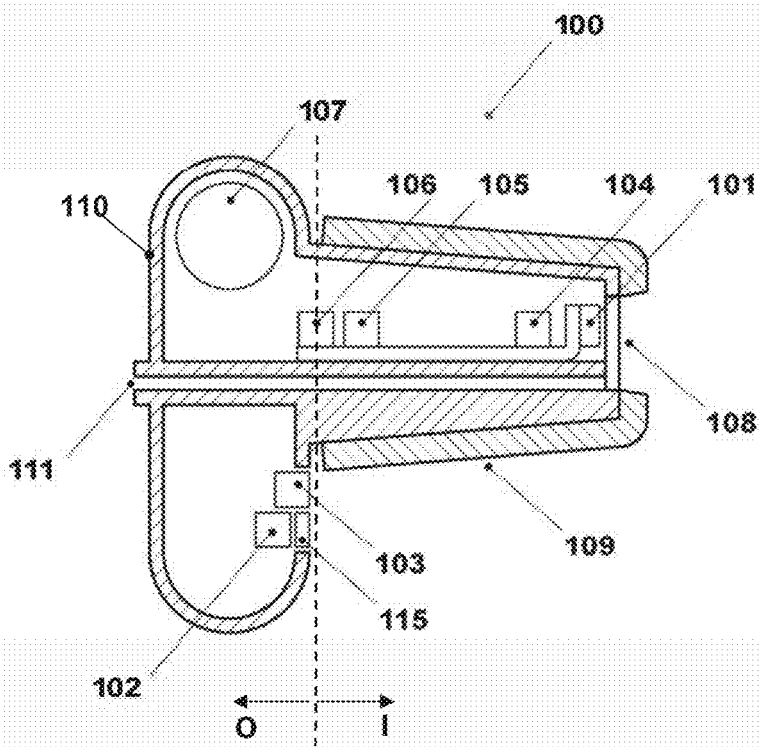
FIG. 4 is a cross-sectional diagram of an earpiece of the monitor of FIG. 3.

FIG. 3 is a schematic diagram of a portable physiology monitor incorporating part of the system of FIG. 1. FIG. 4 is a cross-sectional diagram of an earpiece of the monitor of FIG. 3.

The portable physiology monitor includes an earpiece 100 and a remote wireless device such as a smartwatch 120 or smartphone 130.

The earpiece 100 has a housing 110 generally formed by a single part that is retained in the ear in use and supports multiple sensors and components provided therein. In other embodiments the housing 110 may be assembled from plural, separately formed parts. Nevertheless, the housing 110 can be divided notionally into an inner portion denoted by the arrow marked I in FIG. 4 and an outer portion denoted by the arrow marked O in FIG. 4. The inner portion I is shaped and configured to be inserted into the ear canal and retained therein in use at least in part by a malleable cover 109, formed generally of a compliant and resilient material such as a compressible foam sleeve or a moulded silicone earpiece, as it interfaces with the wearer's ear canal. The outer portion O is shaped and configured to be inserted into the concha of the ear (i.e. the bowl-shaped cavity of the ear located at the entrance to the ear canal) and retained therein in use at least in part by the inner portion I of the housing 110. Optionally, an over-the-ear clip may be provided extending from the outer portion O to be clipped over the pinna of the wearer in use, to further retain the earpiece 100 in place in use.

The earpiece 100 includes a thermopile 101 positioned at the end of the inner part I of the earpiece to measure the temperature of the tympanic membrane as a reference of core body temperature. The thermopile 101 is sized so as to be located and retained inside the housing in the ear canal itself, rather than at an entrance to the ear canal. By locating the thermopile close to the tympanic membrane and sealing it inside the effectively closed environment by the ear insert interfacing with and being retained in the ear canal, the thermopile can be reliably retained in position to sense radiation from the tympanic membrane even during ambulatory use and provide accurate and long term core body temperature measurements in a non-invasive or minimally invasive manner. The thermopile is preferably less than 3 mm by 3 mm in its sensitive plane, even more preferably 2 mm by 2 mm or less. An example of a suitable thermopile for long term in-the-ear use in the earpiece 100 is the Infrared Thermopile Sensor in Ultra Small Chipscale Package TMP006 manufactured by Texas Instruments, Dallas, Tex., USA (http://www.ti.com/product/TMP006#descriptions) that has a package size of only 1.6 mm by 1.6 mm. In some embodiments, the thermopile may be 2 mm×2 mm or less. The thermopile measures the temperature of an object without the need to make contact with the object. This sensor uses a thermopile to absorb the passive infrared energy emitted from the object being measured and uses the corresponding change in thermopile voltage to determine the object temperature. The thermopile voltage is digitized and reported to processor 70 (not shown in FIG. 4) through serial communication. When calibrated and when the signal is smoothed by averaging over a measurement period of, say, a one minute window, the error rate of the thermopile 101 is reduced, and it provides an accuracy of ±0.1 degrees C. The thermopile 101 is provided with an on-board thermistor (not shown) for measuring the die temperature, which is also reported to the processor. The processor can use the reported die temperature and optionally the difference between the die temperature and the temperature detected by the thermopile to reduce the noise floor in the signal reported by the thermopile, giving a higher signal-to-noise ratio. Using a miniaturised thermopile of this type allows the thermopile 101 to be located and retained in the ear canal allowing for improved accuracy and sensitivity of ongoing, ambulatory core body temperature monitoring while also providing space for additional componentry and functionality in the earpiece 100 as will be described below.

The earpiece also includes a pulse oximetry sensor 102, comprising two light emitting diodes and a photo detector positioned in close proximity to one another, to measure pulse rate, pulse volume and oxygen saturation level of blood vessels in the concha of the ear; an ECG sensor 103 positioned to measure the heart's electrical conduction system from the concha of the ear; a respiration sensor 104 to measure breathing vibrations through the inner ear via bone conduction; an accelerometer sensor 105 positioned to measure movement and orientation of a subject's head; and a transceiver 106 arranged to communicate the physiological parameter measurements to a smartwatch 120 or smartphone 130.

The pulse oximetry sensor 102 is positioned directly behind a translucent or transparent window 115, itself positioned in the concha area of the ear.

In alternative embodiments, a respiration sensor 104 may be positioned behind the pinna of ear to detect breathing vibrations via the jaw, which may be provided instead of or in addition to the respiration sensor 104 shown in the embodiment of FIG. 4 provided at the end of the earpiece near the thermopile 101 to detect breathing vibrations via the tympanic membrane.

The ECG sensor 103 comprises two electrodes, which in alternative embodiments may be configured to have one in the concha area and one behind the ear, or where there are two earpieces used as a pair, one in each earpiece in the concha area.

The earpiece 100, smartwatch 120 and smartphone 130 all include one or more batteries to supply power. At least in the case of the earpiece 100, it is preferred that the battery 107 is rechargeable from within the earpiece via a suitable connection to a power-source or inductive coupling to a power-source. In order to conserve battery power, the transceiver 106 may only operate periodically. The earpiece 100, smartwatch 120 and smartphone 130 may include a sleep mode to further conserve power when not in use.

The smartwatch 120 and smartphone 130 include a transceiver arranged to receive measurements from the earpiece, a processor to perform calculations and a display 90 to provide the subject with feedback on the status of one or more of the aforementioned physiological parameters. Preferably, the monitor operates on a substantially real-time basis. Preferably, the transceiver 106 communicates via a wireless data protocol such as BlueTooth™ Low Energy or another suitable wireless communication system.

A disposable or cleanable wax gauze 108 prevents wax and other foreign objects entering the earpiece.

A malleable cover 109 around the body of the earpiece 100 ensures comfort and a good fit for the subject. The cover 109 may be a custom or generic mould and may be provided in different sizes to ensure best fit and comfort. The cover 109 may include a recessed channel to enable ambient sound to reach the subject's inner ear to ensure no loss of hearing or situational awareness, and also to allow the circulation of air to prevent moisture build-up in the auditory canal during exercise. The circulation of air may be the only reason to include the recessed channel, to allow for heat and air transfer, even in applications where ambient sound transmission is not required.

The malleable cover 109 may be removable and interchangeable/replaceable allowing the use of the earpiece for vital signs monitoring for successive patients in remote, residential, clinical and palliative care settings and surgical settings for successive patients in a hygienic, non-invasive or minimally invasive manner.

In one embodiment of the present invention an audio feed-through channel 111 may be provided to enable a tube from an audio generating device to be attached to the earpiece 100 and relay the audio to the subject's inner ear.

The audio feed-through channel 111 may be formed by the housing 110 and configured as a waveguide to provide sound to the inner ear. The output of the audio feed-through channel 111 opening into the ear canal in use is arranged adjacent to the thermopile 101. In the embodiment shown in FIG. 4, the audio feed-through channel 111 is not coupled to any active audio generating source but merely opens to the ambient environment to allow passive throughput of ambient sound to facilitate the situational awareness of the wearer.

Figure 5:
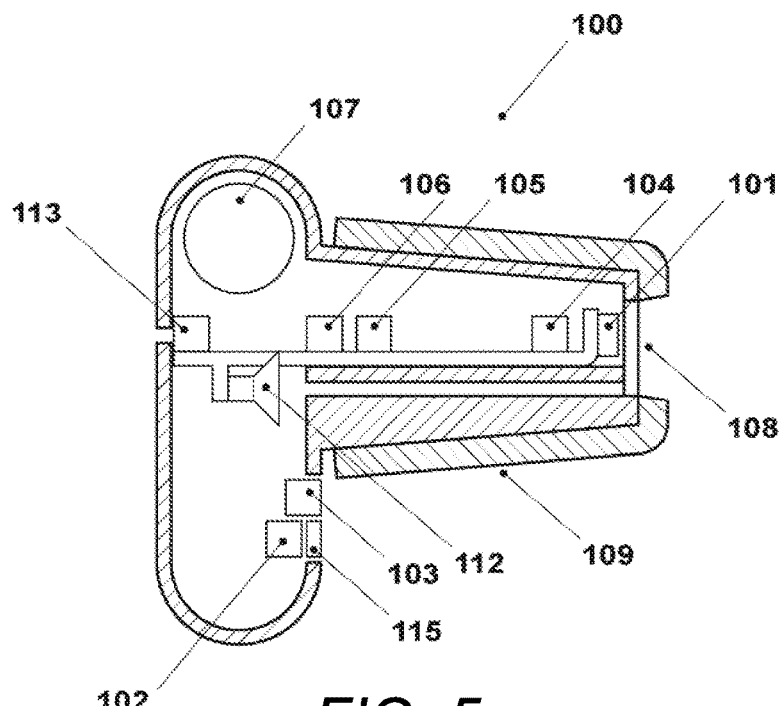
FIG. 5 is a cross-sectional diagram of a further embodiment of an earpiece of the monitor of FIG. 3; and, FIG. 6 is a cross-sectional diagram of an alternative configuration of the earpiece of FIG. 5.

FIG. 5 is a cross-sectional diagram of a further embodiment of an earpiece of the monitor of FIG. 3. As an alternative to the audio feed-through channel 111, active audio may be provided by a speaker 112. A microphone 113 may be used in conjunction with the speaker 112 to record ambient noise and either provide noise cancellation or amplify ambient sound to boost the subject's hearing, as in a hearing aid. Alternatively, an audio signal, such as music or speech, may be provided to the speaker 112, for example via a BlueTooth™ connection between the transceiver 106 and the smartwatch 120 or smartphone 130, and played to the wearer through the audio feed-through channel 111.

Where a speaker 112 is provided, status feedback of the aforementioned physiological parameters may be provided audibly as well as or instead of via the display 90. When a predetermined parameter level is reached and/or intervention is required an alert may sound via the speaker 112 and display 90.

Figure 6:
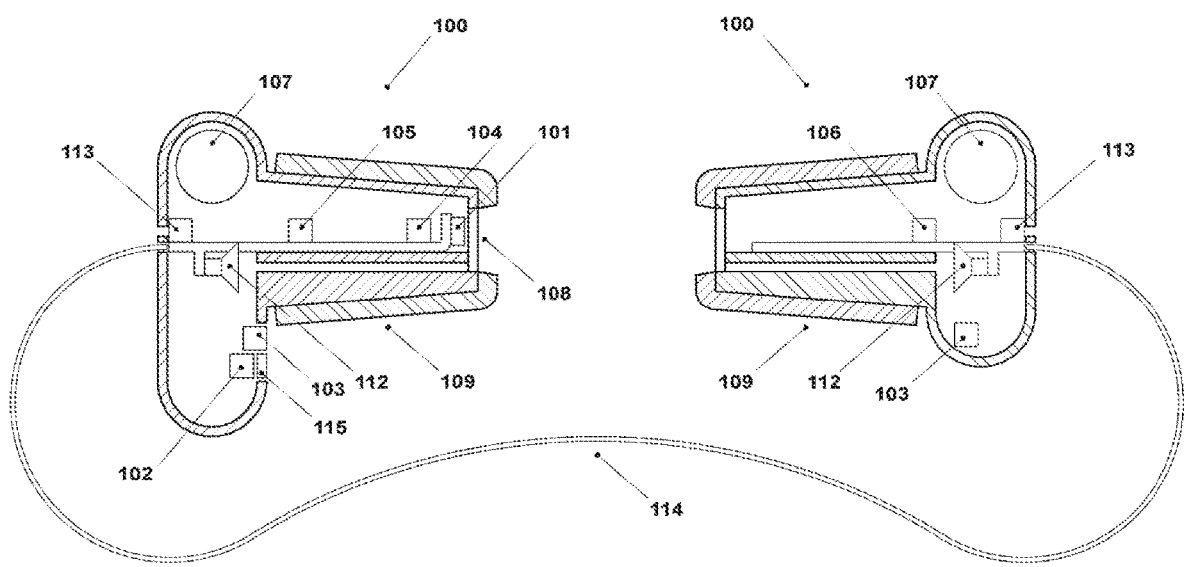

FIG. 6 is a cross-sectional diagram of an alternative configuration of the earpiece of FIG. 5. Where an earpiece 100 is used singly, a speaker 112 can provide mono sound which is useful for communications and feedback status. In an alternative embodiment, the earpiece 100 can be configured as a pair of earpieces to provide stereo sound output for music playback or improved quality of communications sound output by utilising two speakers 112. In this configuration a cable/leash 114 may connect the two earpieces and provide an electrical connection to share power between the earpieces and enable optimized sharing of components between the two earpieces. The leash 114 would also serve as a convenient way to prevent losing one earpiece 100 and could provide a method of securing the earpieces 100 to a garment if provided with a clip.

As the thermopile 101 is a bare silicon die it will be susceptible to thermal radiation signals which appear pretty much anywhere within a 180 degree field of view (subject to an approximate $\cos^2\theta$ weighting to the sensitivity). The temperature of the ear canal is typically different to that of the tympanic membrane and so not a true measure of the core temperature of the body. As the target object, the eardrum, has a radius ~4 mm, and the earpiece 100 is arranged such that the thermopile 101 is likely to be ~15 mm away from the eardrum along the canal, this would mean that the actual eardrum would make up a relatively small fraction of the field of view. Thus, to provide an improved accuracy of the temperature signal obtained from the thermopile 101, this temperature effect should be compensated for.

Figure 7:
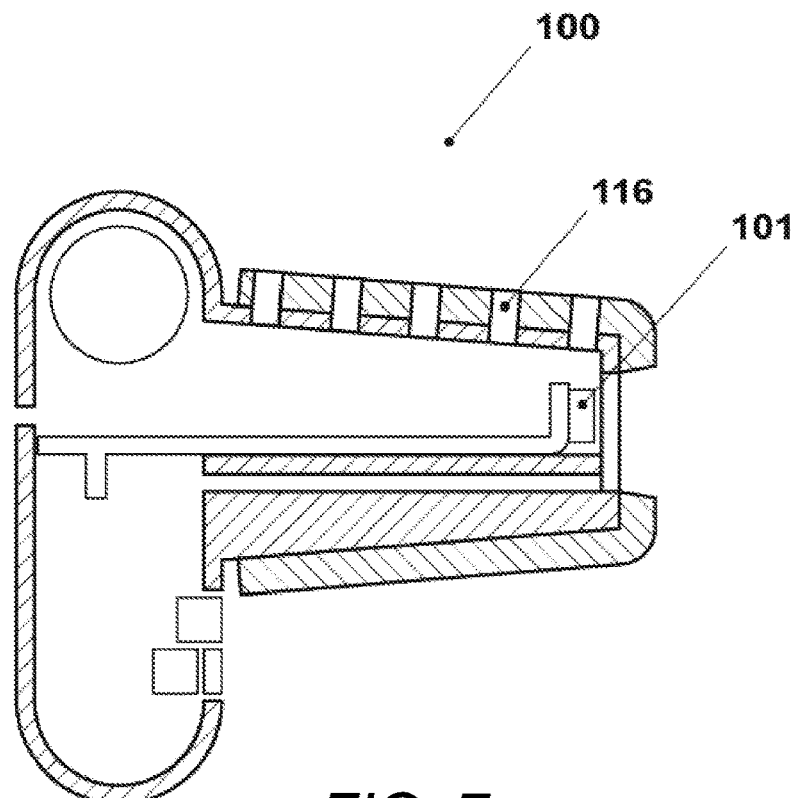
FIG. 7 is a schematic diagram of a portable physiology monitor incorporating a calibration technique.

FIG. 7 is a schematic diagram of a portable physiology monitor incorporating a calibration technique. The earpiece 100 may be configured to incorporate thermistors 116 positioned on or near the outer surface of the earpiece to measure the temperature of the auditory canal wall at numerous depths, from outer ear to tympanic membrane, to create a temperature gradient map of the auditory canal to further compensate for infra-red heat from the auditory canal which may contaminate the tympanic membrane signal received by the thermopile 101. The thermistors 116 may also be used to help ensure the earpiece is placed at the correct depth in the auditory canal in relation to the distance from the outer ear, by checking the measured temperature is in the temperature range of the auditory canal as opposed to the environmental temperature. The thermistors 116 would in this case also serve to alert the processor that the device is situated in the subject's auditory canal and measurements will correspond to the ear. Equally they would alert the processor when the earpiece is removed from the subject either temporarily or at the end of use.

Alternatively to the thermistors 116, capacitive sensors may be used for the same function of detecting if the device is inserted in the auditory canal, and positioned at the correct depth. Contact and conductance of the capacitive sensors against the wall of the auditory canal would enable this functionality.

Figure 8:
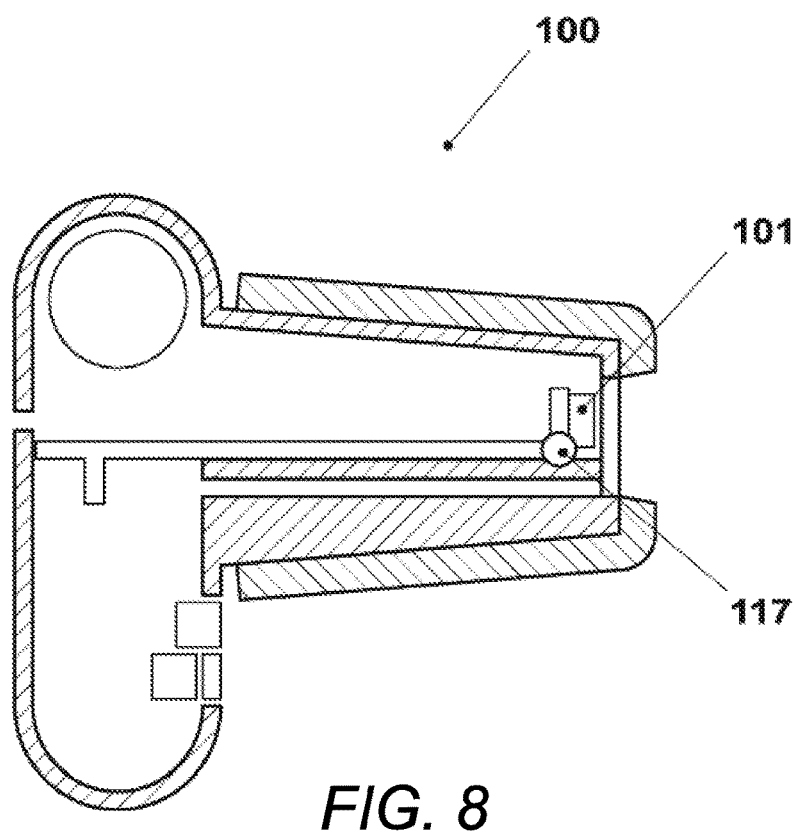
FIG. 8 is a schematic diagram of a portable physiology monitor with adjustable angle of incidence of a sensor.

FIG. 8 is a schematic diagram of a portable physiology monitor with adjustable angle of incidence of a thermopile sensor 101. To enable adjustment of the thermopile 101 angle in respect to line of sight of the tympanic membrane to ensure greatest accuracy, the earpiece 100 may incorporate a pivoting head 117 or other mechanism which could be adjusted during setup of the device on the subject when the earpiece is positioned in the auditory canal. The processor would be configured to alert the subject or clinician when the hottest temperature was measured, indicating the optimal angle of the thermopile 101.

Figure 9:
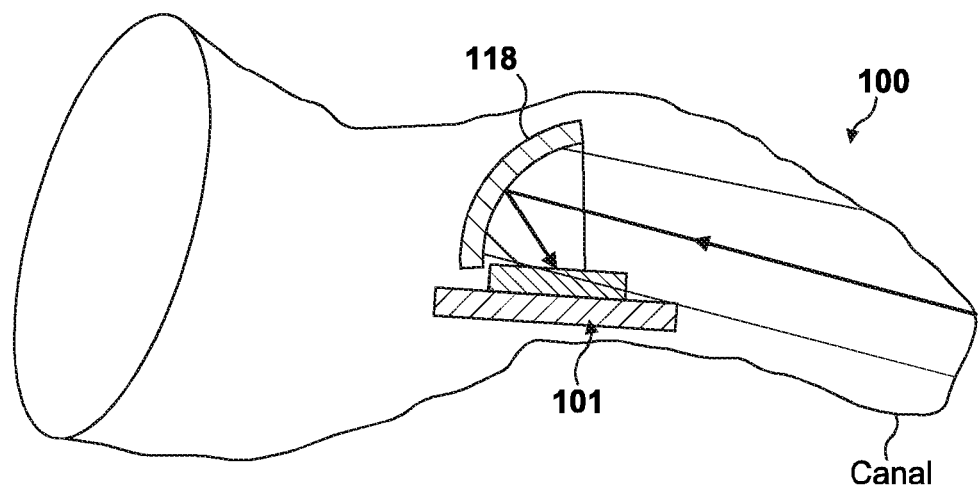
FIG. 9 is a diagram of a portable physiology monitor with a concave reflector in accordance with an embodiment of the present invention.

FIG. 9 is a diagram of a portable physiological monitor with a concave reflector in accordance with an embodiment of the present invention.

In this particular embodiment, for simplicity, the thermopile 101 is shown in isolation in its location in use in the ear canal together with a concave reflector 118, with the remainder of the components of the earpiece not shown. In this particular embodiment, the thermopile 101 is provided substantially parallel to the wall of the housing 110 or the axis of the audio feed through channel 111. Generally, the sensitive surface of the thermopile 101 is not facing the open end of the earpiece housing 110 configured to be provided adjacent to the tympanic membrane of a user, but instead is arranged at an angle oblique or orthogonal thereto. This may serve to reduce the cross-sectional extent of the thermopile 101 in the ear canal, providing more space inside the inside part I of the earpiece 100. The earpiece 100 is further provided with a concave mirror 118 arranged to direct the infrared radiation emitted from the tympanic membrane onto the thermopile 101. The concave mirror 118 reflects and focuses rays of infrared radiation from the direction of the tympanic membrane towards the sensitive surface of the thermopile 101. The concave mirror 118 is shaped and serves to restrict the field of view to that generally in the direction of the tympanic membrane in use, increases the collecting area of the radiation and so improves the signal strength and accuracy of the temperature measurements produced by the thermopile 101 in use. When positioned in the ear canal by an ear insert configured to reliably retain the thermopile and reflector in position, this can provide a reliable signal of the tympanic temperature, with less signal contribution from the ear canal.

Figure 10:
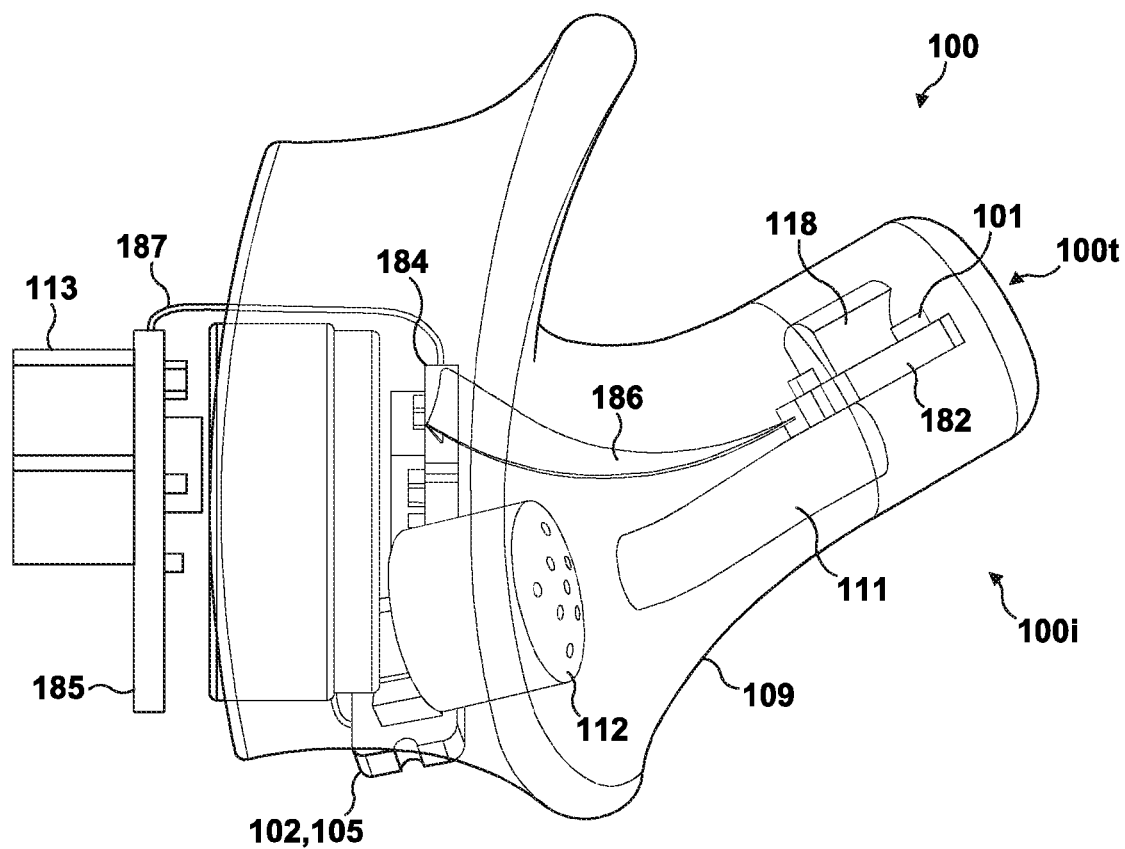
FIG. 10 shows a portable physiological monitor in accordance with an embodiment of the present invention.

FIG. 10 shows a portable physiological monitor in accordance with an embodiment of the present invention.

The portable physiological monitor is in the form of a wearable device in the form of an earpiece 100 comprises a housing 110 and an ear insert portion 100i covered by a retaining portion 109 configured to extend in and substantially fill the lateral expanse of the ear canal by virtue of having been molded to the shape of the ear of the wearer, or by virtue of being formed of a resilient material that deforms to the shape of the ear of the wearer. The retaining portion 109 is arranged to retain the housing 110 in the ear canal, in use. The earpiece 100 further comprises a thermopile module 100t comprising an earpiece housing portion supporting an inner ear PCB 182, itself comprising a thermopile 101 and a concave reflector 118 substantially as described with reference to FIG. 9 previously. In other embodiments, the thermopile arrangement for picking up infrared signals from the tympanic membrane may differ from that shown in FIG. 9. The inner ear PCB 182 is connected to a first outer PCB 184 with a first flexible PCB 186 providing a wired 'umbilical' electrical connection to the inner ear PCB 182. The first outer PCB 184 is connected to a second outer PCB 185 with a second flexible PCB 187. The first outer PCB 184 comprises a speaker 112, a pulse oximetry sensor 102 and an accelerometer sensor 105. The second outer PCB 185 comprises an ambient microphone 113. An audio feed through channel 111 is provided by an audio cavity opening into the ear canal in use by an output defined adjacent to the thermopile 101 whereby to allow audio to propagate past the thermopile 101 towards the tympanic membrane. The audio feed through channel 111 receives audio from the speaker 112 which is configured to produce audio received by the microphone 113. It will be appreciated that the speaker 112 may additionally or alternatively produce audio received from other sources. The reliable retaining of the thermopile module 100t in position by an ear insert 100i extending in and substantially filling the ear canal in use allows the tympanic temperature to be reliably measured in a manner that is comfortable and amenable to the wearer. The provision of the audio passageway extending through the ear insert and opening into the ear canal in use permits sound to be provided to the inner ear of the wearer in use. Optionally, the audio passageway substantially surrounds or in embodiments, envelops or includes or is concentric with the wired electrical connection, allowing an even more compact construction and a better use of space. Typically the thermopile module 100t is positioned in the ear canal in a generally centralised position by the ear insert 100i retaining portion 109, with the audio passageway output then being in the region of the thermopile module 100t, to the side thereof or rearwards thereof so as to output sound into the ear canal. The positioning of the thermopile module 100t to obtain a signal primarily from the tympanic membrane is thus not compromised by the provision of the audio passageway, which is configured to open into the ear canal in the region of the thermopile module 100t to provide sound to the inner ear in use. In this respect, the thermopile module 100t may be reliably retained in a 'central' position within the ear canal at or near the second bend in the ear canal behind which the tympanic membrane is positioned. The ear insert and thermopile module are shaped and dimensioned to be positionable close to the second bend in the ear canal, with the thermopile module being preferably less than 4 mm across in its largest lateral dimension, even more preferably less than 3.5 mm in diameter. To allow the accurate positioning of the thermopile module, the thermopile module 100t may extend at least partially forwardly from the retaining portion 109 at the innermost end of the ear insert. The ear insert 100i and the thermopile module 100t may be oval-shaped in the region of the innermost end thereof. The output of the audio passageway is located to the side of, or adjacent, the centred position of the thermopile module. The audio passageway output may open to the rear of the temperature sensor module, particularly where the audio passageway at least partially surrounds the wired electrical connection from the thermopile module 100t. These arrangements provide an effective use of space to allow sound to be provided to the inner ear through the ear canal which is substantially filled with an ear insert retaining portion 109 to accurately position the thermopile module 100t to receive a signal from the tympanic membrane.

Figure 11:
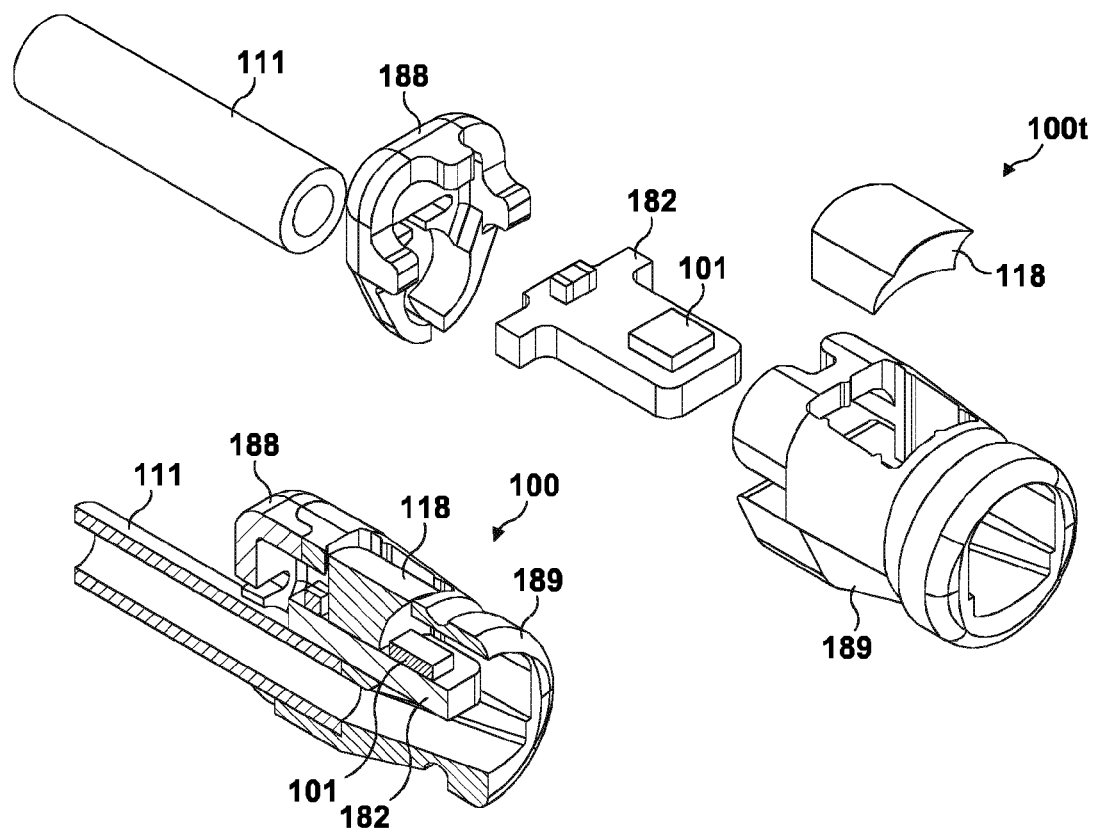
FIG. 11 shows an exploded view and an assembled diagram of an alternative embodiment of the portable physiological monitor shown in FIG. 10.

FIG. 11 shows an exploded view and an assembled diagram of an alternative embodiment of the thermopile module 100t of the portable physiological monitor shown in FIG. 10 and is substantially as described with reference to FIG. 10, apart from the hereinafter described differences. The housing 110 is formed from a cap piece 188 and an inner body piece 189. Note that only the inner body of the earpiece 100 is shown. As can be seen, the modular construction of the FIG. 11 and also the FIG. 10 design allows a relatively simplified manufacturing and assembly process, with a minimal number of parts.

Figure 12:
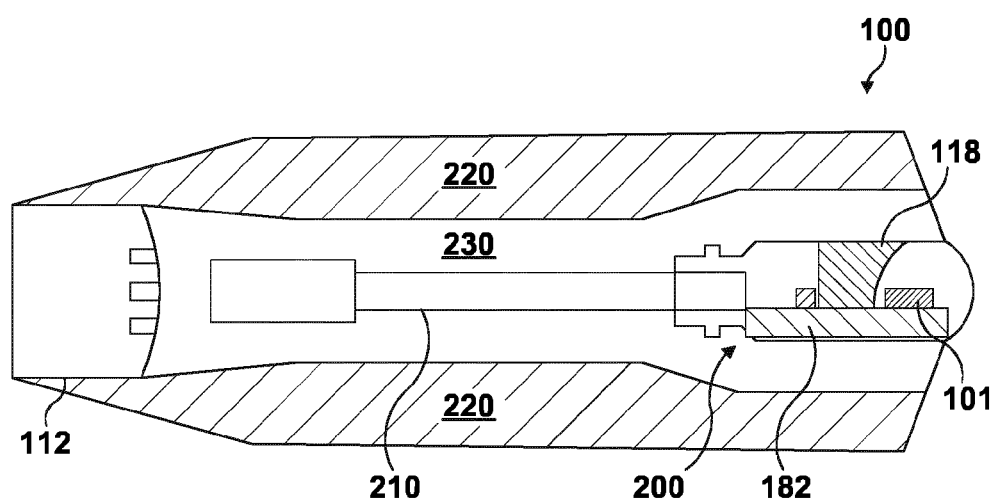
FIG. 12 shows a schematic diagram of a physiological monitor in accordance with an embodiment of the present invention.

FIG. 12 shows a schematic diagram of an embodiment of a wearable device in accordance with an aspect of the present invention. The wearable device 100 comprises an ear insert comprising a retaining portion 220 formed by molding or from a resilient material so as to be shaped in use to conform to and substantially fill the ear canal of the wearer and to extend along the ear canal retain the wearable device 100 within the ear canal. The ear insert further comprises a thermopile module 200 configured to be provided at an innermost end of the ear insert. The retaining portion 220 extends in the ear canal up to the thermopile module 200. The thermopile module 200 comprises a housing and is connected to further electrical components, for example a battery (not shown) through an electrical connection in the form of an umbilical cable 210. The thermopile module 200 further comprises an infrared thermopile 101 and a reflector 118 as described previously. A speaker 112 is also provided as part of the wearable device 100. The ear insert further comprises an audio conduction channel provided by an audio passageway 230 defined within the retaining portion 220 of the ear insert whereby to allow sound to pass from the speaker 112 through the retaining portion 220 and beyond the thermopile module 200 towards the tympanic membrane.

In this particular embodiment, the audio passageway 230 surrounds the umbilical cable 210. This configuration means only one passageway through the retaining portion of the ear insert 220 is required to convey both sound and the signals from the infrared thermopile. The output of the audio passageway 230 is also to the side of and surrounds the thermopile module 200 to open into the ear canal slightly to the rear of the forward end of the thermopile module 200. These such arrangements represent an effective use of space and allows the reliable and accurate positioning of the thermopile in the inner ear close to the tympanic membrane while also allowing sound to be provided to the inner ear in a space-constrained environment.

When inserted into a subject's auditory canal, the thermopile 101 detects incident infrared radiation from the tympanic membrane and provides a voltage equivalent to the core body temperature of the subject. Preferably, the processor converts this into a temperature reading in degrees Centigrade or Fahrenheit.

When placed in the concha, the pulse oximetry sensor 102 detects the oxygen saturation level and volume of a subject's pulse through the transmittance of red and infra-red light through tissue. Preferably, the processor converts this into a reading of pulse rate, pulse volume and oxygen saturation level. In some embodiments a blood pressure cuff may be used in conjunction with the pulse oximetry sensor to provide pulse pressure readings and/or calibrate the pulse oximetry sensor. Preferably, the result is pulse rate in beats per minute, pulse pressure and pulse volume in millimetres of mercury, and oxygen saturation as a percentage. In some embodiments the result may also output a plethysmogram.

As an alternative to, or in addition to, the pulse oximetry sensor 102, embodiments of the present invention may incorporate a piezoelectric monitoring system for measuring pulse rate and pressure from the temporal artery. The system comprises a cuff to occlude the artery and a piezoelectric contact microphone to record and analyse the Korotkoff sounds from the change in pulse.

When placed in the concha, the ECG sensor 103 detects the heart's electrical conduction system. Preferably, the processor converts this into an ECG reading in millivolts per second.

When inserted into a subject's auditory canal, the bone conduction microphone 104 detects breathing vibrations through the inner ear. Preferably, the processor converts this into a respiration rate in breaths per minute. The bone conduction microphone may be provided in and supported by the thermopile module 100*t*, 200.

The accelerometer 105 monitors the movement and orientation of a subject. Preferably, the processor converts this into a reading of one or more of the cadence, speed, distance, orientation and calorific count of a subject, and the result is in revolutions or strokes per minute, kilometres per hour or miles per hour, metres or kilometres or miles, degrees, and calories or kilocalories per hour, respectively. In some embodiments the data may also be used in combination with core body temperature to provide an indication of the circadian rhythm of a subject, wherein the result is preferably of time in hours.

Preferably, measured readings are input to the earpiece processor and periodically relayed to the subject in real-time via the earpiece speaker 112, if present and configured by the user, as well as transmitted to a remote device such as smartwatch 120 and smartphone 130 where the on-board processor and software application output the measured readings in a text and graphical form to the subject via the display 90.

Preferably, the earpiece stores the measured readings in its internal memory until, or unless, it has paired with a remote device, in which event the measured readings are transmitted wirelessly to the remote device and stored in the memory of the remote device for a limited period, accessed through the software application. In some embodiments the data may be uploaded to the cloud (internet) where the subject can store their data in a user account in addition to the remote device for longer term storage, again accessed by the software application on the remote device. In both cases the subject can subsequently access their physiology data from one or more previous sessions for analysis.

The primary device (earpiece) is not dependent on the remote device and the remote device is not necessarily required for the subject to be informed and/or alerted of their vital signs measurements, but if present will be dependent on the primary unit.

Preferably, the physiological parameters of the subject will be measured at specific intervals, or at intervals selectable by the subject from a pre-determined list between, for example, 1 second to 15 minutes (1 second, 5 seconds, 15 seconds, 30 seconds, 1 minute, 5 minutes, 15 minutes). For each interval, the samples recorded during that time period will be averaged, and the average measurement will be communicated to the subject and/or other individual by audio and/or visual means as described above. If any physiological parameter of the subject as measured by the device reaches the safety limits of measurement, the primary device and/or remote device will alert the subject and/or other individual immediately upon reaching this limit by audio and/or visual means, regardless of the chosen interval time. Preferably, the subject and/or other individual will also have the ability to choose their own parameter limits from a pre-determined list, which would exist inside the limit of measurement of the primary device.

Depending on the configuration of the earpiece and smartwatch and/or other remote unit, the subject may be able to select between a choice of a sound or vibration alert, or both.

Various embodiments may eventually be produced to cater for the various needs of:

a. Professional and amateur athletes and sportsmen/women (and novice sports persons);
  b. sports medicine research;
  c. exercise physiology;
  d. military personnel (Army, Royal Navy and Royal Air Force, special forces);
  e. police officers;
  f. firefighters;
  g. those in occupational health and at risk of exertional heat or cardiovascular illness (bakery workers, farmers, construction workers, miners, boiler room workers, factory workers);
  h. company executives;
  i. elderly and infirm;
  j. medical patients (inpatients and pre- or post-operative outpatients);
  k. healthcare telemedicine;
  l. mentally and chronically ill;
  m. domestic healthcare including all individuals;
  n. paediatrics; and,
  o. normal public users For example, whilst athletes may be interested in actual numeric levels, the public users may prefer an indicator in the form of a traffic light or similar (for example, green=physiological parameter normal, amber=physiological parameter a little compromised, red=subject reaching illness). Similarly, hospital patients themselves may not take interest in or understand their physiology status but the output data could be passed to medical staff for analysis and intervention of treatment or it may be fed into a control system for automatic regulation of the measured physiological parameters of a patient, where appropriate. Some embodiments may include a memory and connection/transmission system so that data can be recorded over time and uploaded onto a computer for more detailed analysis of physiological status and/or performance.

An example embodiment of the present invention that may be used by clinicians or other medical personnel, safety officers or trainers/coaches of sportsmen is shown in FIG. 2 in which the earpiece 100 may have additional functionality and communicate with a hub or base station 160. As the base station is not required to be portable, it can include a larger display and/or more powerful speaker and a transceiver having a greater reception radius to allow the subject to move further from it and still be in contact. The base station could be used in conjunction with a smartwatch or other remote device so both a subject and the safety officer or other supporting individual are able to see the data of the physiological parameters; indeed, there may even be provided different types of information depending on specific needs.

Data from the accelerometer and other aforementioned sensors may also be processed to determine the circadian rhythm of the subject, and this information could be used for several purposes including the detection and management of dementia and sleep and behavioural disorders. Some embodiments may further include an ambient light sensor to measure the ambient light of the subject's environment and better predict or determine the circadian rhythm of the subject.

The processor may execute instructions stored in memory to instantiate a blood pressure estimation module arranged to accept measurements from a combination of two or more of: pulse sensor, a motion sensor for ballistocardiography (BCG) and an ECG sensor, to calculate changes in pulse transit time (PTT), and to generate from the pulse transition time, a measure of pulse wave velocity and an estimation of relative blood pressure. Alternatively, the raw pulse sensor, BCG and/or ECG data may be sent from the wearable device to another device such as a smartphone or smartwatch which may itself provide a blood pressure estimation module.

The device may also be used to predict or determine the menstrual cycle of a female subject, including determining such physiological parameters as the ovulation day, fertile period, infertile period, onset and/or end of menstruation, menstruation period, start and/or end days of the cycle, and any other day of the cycle. By measuring the basal core body temperature daily at the same time each day, the processor can be arranged to determine the day of ovulation from the largest difference in basal core body temperature elevation. With this data and the subject inputting the first day of menstruation, all other parameters can be determined, and used for predictions of future menstruations, and act as a pregnancy aid.

Data from the pulse oximetry sensor may be used to assist in fitness training of a subject, since it is known that there are several heart rate zones in which maximum fitness benefit can be achieved for different fitness needs.

The device may also be used to prevent athletes reaching their 'ceiling temperature' and fatigue, for example, an ultra endurance event where the athlete is performing at their peak for several hours. An indication of extreme temperature would allow the athlete to reduce their effort and continue exercising rather than reaching fatigue and having to stop exercising or even collapse. This would apply even if there was no water available for rehydration. Therefore, by using the device they don't lose valuable time in competition, and can reduce the risk of heat illness and physiological harm.

In addition, core body temperature and heart rate measurements combined with data from the accelerometer may be used to determine the hydration status of a subject. Since an increase in core body temperature and heart rate at constant workload is indicative of a dehydrating state, hydration status can be predicted and alerts sent to the wristwatch and/or other remote device to prevent the subject from becoming dehydrated or suffering from heat illness.

Thus the various vital signs monitored using the earpiece 100 can be combined and a number of different ways to provide an indication of a state of health or exercise of the wearer.

In a further embodiment, particularly in healthcare with multi-use earpieces, the earpiece may incorporate a disposable or cleanable lens cover and or filters specifically designed to fit the earpiece to prevent dirt or body tissue and wax ingress and build up on the earpiece and cross-contamination when used on multiple subjects.

It will be appreciated that in some embodiments of the invention, functions described as being performed by a processor located outside the earpiece, for example, in a smartwatch or smartphone, may instead be performed by a processor provided as part of the wearable device, and in particular as part of the earpiece. Where a processor is provided in the wearable device, it will also be appreciated that a memory may also be provided for storing instructions executable by the processor.

For example, the wearable device may comprise a blood pressure estimation module arranged to accept measurements from a combination of two or more of: pulse sensor, a motion sensor for ballistocardiography (BCG) and an ECG sensor, to calculate changes in pulse transit time (PTT), and to generate from the pulse transition time, a measure of pulse wave velocity and an estimation of relative blood pressure. A processor in the wearable device may be used to perform the steps necessary for the blood pressure estimation module.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

The invention claimed is:

1. A wearable device for measuring a tympanic temperature, the wearable device comprising:
    an ear insert comprising a housing that extends along and is retained within an ear canal when in use by a retaining portion covering the ear insert, the ear insert comprising:
        a thermopile module housing portion arranged at an innermost end of the housing, supporting an infrared thermopile arranged for measuring a tympanic temperature when in use;
        a wired electrical connection extending through the ear insert and configured to output a signal from the infrared thermopile when in use; and
        an audio conduction channel defined at least partially within the ear insert housing and configured as a waveguide to relay sound toward a tympanic membrane when in use, wherein an output of the audio conduction channel is provided in the side of the housing opening into the ear canal to the rear of and lateral to the thermopile module.

2. The wearable device as claimed in claim 1, wherein the wired electrical connection is at least partially located within the housing and lateral to at least a portion of the audio conduction channel.

3. The wearable device as claimed in claim 1, wherein the audio conduction channel is configured as a passive waveguide to relay sound from at least one of: an audio driver or an ambient environment.

4. The wearable device as claimed in claim 1, further comprising:
    an audio driver electrically connected to an audio input configured to drive the audio driver to output sound to the audio conduction channel.

5. The wearable device as claimed in claim 4, further comprising a microphone arranged to receive sound from outside an ear that comprises the tympanic membrane, wherein the audio input is configured to be provided by a signal derived from the microphone.

6. The wearable device as claimed in claim 1, wherein the thermopile module is disposed at a centered position with respect to an opening at an innermost end of the ear insert.

7. The wearable device as claimed in claim 1, wherein the thermopile module has a cross section of less than four millimeters.

8. The wearable device as claimed in claim 1, further comprising a plurality of portions that are configured to connect together to hold in place the audio conduction channel and the infrared thermopile.

9. The wearable device as claimed in claim 1, wherein:
the thermopile module comprises a reflector that comprises a concave reflecting surface facing an opening of an innermost end of the ear insert and configured to reflect, onto the infrared thermopile, infrared radiation received via the opening; and
the infrared thermopile is oriented to detect the infrared radiation received from the reflector.

10. A wearable device for measuring a tympanic temperature, the wearable device comprising:
an ear insert comprising a housing that extends along and is retained within an ear canal when in use by a retaining portion covering the ear insert, the ear insert comprising:
a thermopile module housing arranged at an innermost end of the housing, supporting an infrared thermopile configured to measure a temperature of a tympanic membrane when the housing is retained within the ear canal;
a wired electrical connection extending through the ear insert and configured to output a signal from the infrared thermopile when in use; and
an audio conduction channel at least partially extending through the ear insert and configured as a waveguide to relay sound toward the tympanic membrane when the housing is retained within the ear canal, wherein an output of the audio conduction channel is provided at the side of the housing opening into the ear canal to the rear of and lateral to the thermopile.

11. The wearable device as claimed in claim 10, wherein the wired electrical connection is at least partially located within the housing and lateral to at least a portion of the audio conduction channel.

12. The wearable device as claimed in claim 10, wherein the audio conduction channel is configured as a passive waveguide to relay sound from at least one of: an audio driver or an ambient environment.

13. The wearable device as claimed in claim 10, further comprising:
an audio driver electrically connected to an audio input configured to drive the audio driver to output sound to the audio conduction channel.

14. The wearable device as claimed in claim 13, further comprising a microphone arranged to receive sound from outside an ear that comprises the tympanic membrane, wherein the audio input is configured to be provided by a signal derived from the microphone.

15. The wearable device as claimed in claim 10, wherein the thermopile module is disposed at a centered position with respect to an opening at an innermost portion of the ear insert.

16. The wearable device as claimed in claim 10, wherein the thermopile module has a cross section of less than four millimeters.

17. The wearable device as claimed in claim 10, further comprising a plurality of portions that are configured to connect together to hold in place the audio conduction channel and the infrared thermopile.

18. The wearable device as claimed in claim 10, wherein:
the thermopile module comprises a reflector that comprises a concave reflecting surface facing an opening of an innermost portion of the ear insert and configured to reflect, onto the infrared thermopile, infrared radiation received via the opening; and
the infrared thermopile is oriented to detect the infrared radiation received from the reflector.

* * * * *